United States Patent
Maxik

(10) Patent No.: US 7,824,065 B2
(45) Date of Patent: Nov. 2, 2010

(54) SYSTEM AND METHOD FOR PROVIDING MULTI-FUNCTIONAL LIGHTING USING HIGH-EFFICIENCY LIGHTING ELEMENTS IN AN ENVIRONMENT

(75) Inventor: Fredric Maxik, Plantation, FL (US)

(73) Assignee: Lighting Science Group Corporation, Dallas, TX (US)

( * ) Notice: Subject to any disclaimer, the term of this patent is extended or adjusted under 35 U.S.C. 154(b) by 960 days.

(21) Appl. No.: 10/915,137

(22) Filed: Aug. 9, 2004

(65) Prior Publication Data

US 2005/0207159 A1    Sep. 22, 2005

Related U.S. Application Data

(60) Provisional application No. 60/554,469, filed on Mar. 18, 2004, provisional application No. 60/565,268, filed on Apr. 23, 2004, provisional application No. 60/567,082, filed on Apr. 30, 2004, provisional application No. 60/567,226, filed on Apr. 30, 2004.

(51) Int. Cl.
*F21V 33/00* (2006.01)
*F21V 4/00* (2006.01)

(52) U.S. Cl. .................. 362/234; 362/249.02; 362/287; 703/1

(58) Field of Classification Search ................ 362/225, 362/252, 293, 317, 221, 217.1, 217.14–217.17, 362/227, 234, 236, 249.01, 249.02, 282, 362/287; 703/1, 13, 4
See application file for complete search history.

(56) References Cited

U.S. PATENT DOCUMENTS 2,981,827 A    4/1961  Orsatti et al.

| 4,136,378 A | 1/1979 | Chevali |
| 4,211,955 A | 7/1980 | Ray |
| 4,243,934 A | 1/1981 | Brasfield |
| 4,423,473 A | 12/1983 | Kirkley |
| 4,455,562 A | 6/1984 | Dolan et al. |
| D302,863 S | 8/1989 | Krol |

(Continued)

FOREIGN PATENT DOCUMENTS

DE    101 05 622 A1    8/2002

(Continued)

OTHER PUBLICATIONS

Fredric S. Maxik and Addy S. Widjaja, U.S. Appl. No. 29/285,243, filed Mar. 23, 2007, for "LED Light Bulb".

(Continued)

*Primary Examiner*—Thuy Vinh Tran
(74) *Attorney, Agent, or Firm*—Cantor Colburn LLP

(57) ABSTRACT

A system and method for providing multi-functional lighting in a lighting system in an environment is disclosed. The system uses high-efficiency lighting elements for providing multi-functional lighting in the environment. The types and quantity of high-efficiency lighting elements is determined based upon information entered provided to the system by a user according to their functional desires for the environment. Among the functions provided to the environment include: lighting, bacteriological control, biological control, pest control, and pollution control. In one embodiment of the high-efficiency lighting elements are light emitting diodes (LEDs). In one embodiment of the multi-functional lighting system, the system further determines location of the lighting elements to be used within the environment based on the information provided by a user.

19 Claims, 12 Drawing Sheets

U.S. PATENT DOCUMENTS

| | | |
|---|---|---|
| D325,994 S | 5/1992 | Hume et al. |
| 5,136,483 A | 8/1992 | Schoniger |
| 5,162,696 A | 11/1992 | Goodrich |
| 5,175,528 A | 12/1992 | Choi et al. |
| D336,963 S | 6/1993 | Levin et al. |
| 5,313,187 A | 5/1994 | Choi et al. |
| 5,358,880 A | 10/1994 | Lebby |
| D355,495 S | 2/1995 | Matsumura et al. |
| 5,439,941 A | 8/1995 | Butler et al. |
| 5,561,346 A | 10/1996 | Byrne |
| 5,585,783 A | 12/1996 | Hall |
| 5,707,132 A | 1/1998 | Ooki et al. |
| 749,646 A | 5/1998 | Brittell |
| D395,092 S | 6/1998 | Vakil |
| 5,782,553 A | 7/1998 | McDermott |
| 5,877,863 A | 3/1999 | Ross et al. |
| 5,929,788 A | 7/1999 | Vukosic |
| D414,282 S | 9/1999 | Kato et al. |
| 6,016,038 A | 1/2000 | Mueller et al. |
| D426,653 S | 6/2000 | Ho |
| D427,335 S | 6/2000 | Noll |
| D433,166 S | 10/2000 | Noll |
| 6,150,771 A | 11/2000 | Perry |
| 6,150,774 A | 11/2000 | Mueller |
| D435,577 S | 12/2000 | McBride |
| 6,166,496 A | 12/2000 | Lys |
| 6,184,628 B1 | 2/2001 | Ruthenberg |
| 6,211,626 B1 | 4/2001 | Lys |
| 6,220,722 B1 | 4/2001 | Begemann |
| 6,227,679 B1 | 5/2001 | Zhang |
| 6,285,119 B1 | 9/2001 | Sundhar |
| 6,286,969 B1 | 9/2001 | Kurokawa et al. |
| 6,293,684 B1 | 9/2001 | Riblett |
| 6,345,903 B1 | 2/2002 | Koike |
| 6,350,041 B1 | 2/2002 | Tarsa et al. |
| 6,369,781 B2 | 4/2002 | Hashimoto et al. |
| 6,371,636 B1 | 4/2002 | Wesson |
| 6,489,937 B1 | 12/2002 | Ruvinsky |
| D469,890 S | 2/2003 | Bobel |
| D470,606 S | 2/2003 | Bobel |
| D470,608 S | 2/2003 | Bobel |
| D470,610 S | 2/2003 | Bobel |
| 6,523,978 B1 | 2/2003 | Huang |
| 6,547,421 B2 | 4/2003 | Sugano |
| 6,548,967 B1 | 4/2003 | Dowling |
| 6,580,228 B1 | 6/2003 | Chen et al. |
| 6,600,274 B1 | 7/2003 | Hughes |
| 6,608,453 B2 | 8/2003 | Morgan |
| 6,621,222 B1 | 9/2003 | Hong |
| D482,143 S | 11/2003 | Buschmann et al. |
| 6,659,632 B2 | 12/2003 | Chen |
| 6,662,489 B2 | 12/2003 | Spiro et al. |
| 6,674,096 B2 | 1/2004 | Sommers |
| 6,683,419 B2 | 1/2004 | Kriparos |
| 6,697,130 B2 | 2/2004 | Weindorf |
| D487,940 S | 3/2004 | Buschmann et al. |
| 6,707,247 B2 | 3/2004 | Murano |
| 6,709,126 B1 | 3/2004 | Leen |
| 6,709,132 B2 | 3/2004 | Ishibashi |
| 6,724,156 B2 | 4/2004 | Fregoso |
| D490,919 S | 6/2004 | Wiesmeth |
| D491,301 S | 6/2004 | Chen |
| D493,007 S | 7/2004 | Rugendyke et al. |
| 6,767,111 B1 | 7/2004 | Lai |
| D494,687 S | 8/2004 | Matsui et al. |
| D497,439 S | 10/2004 | Shaw et al. |
| D498,310 S | 11/2004 | Gagnon et al. |
| 6,822,397 B2 | 11/2004 | Kawasaki et al. |
| D500,872 S | 1/2005 | Foo |
| D501,055 S | 1/2005 | Packard |
| 6,840,003 B2 | 1/2005 | Moore |
| 6,883,938 B1 | 4/2005 | Kohara et al. |
| D505,738 S | 5/2005 | Buschmann et al. |
| 6,900,781 B1 | 5/2005 | Mori et al. |
| D508,575 S | 8/2005 | Buschmann et al. |
| 6,942,360 B2 | 9/2005 | Chou et al. |
| D514,237 S | 1/2006 | Buschmann et al. |
| 6,982,518 B2 | 1/2006 | Chou et al. |
| D516,229 S | 2/2006 | Tang |
| D528,227 S | 9/2006 | Chou et al. |
| D529,635 S | 10/2006 | Johnson |
| D532,124 S | 11/2006 | Iwase et al. |
| D535,038 S | 1/2007 | Egawa et al. |
| 7,178,941 B2 * | 2/2007 | Roberge et al. ............. 362/225 |
| D542,425 S | 5/2007 | Wang |
| D542,943 S | 5/2007 | Wang |
| D545,457 S | 6/2007 | Chen |
| D546,980 S | 7/2007 | Lo |
| D547,466 S | 7/2007 | Lo |
| 2001/0024112 A1 | 9/2001 | Jacobs et al. |
| 2001/0055353 A1 | 12/2001 | Rybicki et al. |
| 2002/0187570 A1 | 12/2002 | Fukasawa |
| 2003/0031015 A1 | 2/2003 | Ishibashi |
| 2003/0072145 A1 | 4/2003 | Nolan et al. |
| 2003/0090910 A1 | 5/2003 | Chen |
| 2003/0117803 A1 | 6/2003 | Chen |
| 2004/0026683 A1 | 2/2004 | Yamada et al. |
| 2004/0037080 A1 | 2/2004 | Luk et al. |
| 2004/0052076 A1 * | 3/2004 | Mueller et al. ............. 362/293 |
| 2004/0189185 A1 | 9/2004 | Yotsuya |
| 2005/0007304 A1 | 1/2005 | Gallagher et al. |
| 2005/0099108 A1 | 5/2005 | Hofmann et al. |
| 2005/0174769 A1 | 8/2005 | Yong et al. |
| 2005/0248277 A1 | 11/2005 | Van Bruggen et al. |
| 2006/0002110 A1 * | 1/2006 | Dowling et al. ............. 362/252 |

FOREIGN PATENT DOCUMENTS

| | | |
|---|---|---|
| EP | 0 441 965 A1 | 8/1991 |
| EP | 0 617 092 A2 | 3/1994 |
| EP | 0 939 429 A1 | 9/1999 |
| FR | 2 586 844 | 3/1987 |
| GB | 2 345 954 A | 7/2000 |
| GB | 2 366 610 A | 3/2002 |
| JP | 10-305453 | 11/1998 |
| JP | 2000-21209 | 1/2000 |
| JP | 2001 243807 | 9/2001 |
| JP | 2001 325809 | 11/2001 |
| WO | WO 03/017320 A1 | 2/2003 |
| WO | WO 03/034458 A2 | 4/2003 |
| WO | WO 03/059013 A1 | 7/2003 |
| WO | WO 2004/003869 | 1/2004 |

OTHER PUBLICATIONS

Fredric S. Maxik and Addy S. Widjaja, U.S. Appl. No. 29/288,651, filed Jun. 18, 2007, for "LED Light Bulb".

Fredric S. Maxik and Addy S. Widjaja, U.S. Appl. No. 29/295,372, filed Sep. 27, 2007, for "LED Light Bulb".

Fredric S. Maxik, U.S. Appl. No. 29/243,097, filed Nov. 18, 2005 for "LED Light Bulb".

Fredric S. Maxik, U.S. Appl. No. 60/554,469, filed Mar. 18, 2004 for "Lightbulb Using Electronically Activated Light Emitting Elements and Method of Making Same".

Fredric S. Maxik, U.S. Appl. No. 60/565,268, filed Apr. 23, 2004 for "Electronic Light Generating Element Lightbulb".

Fredric S. Maxik, U.S. Appl. No. 60/567,082, filed Apr. 30, 2004 for "Wide Angle Light Dispersion Electronically Activated Lightbulb and Method of Making Same".

Fredric S. Maxik, U.S. Appl. No. 60/567,226, filed Apr. 30, 2004 for "Lightbulb Using Electronic Light Generating Sources".

Fredric S. Maxik and Catherina G.M. Friderici, U.S. Appl. No. 29/224,334, filed Feb. 28, 2005 for "Flashlight".

Fredric S. Maxik and Catherina G.M. Friderici, U.S. Appl. No. 29/224,333, filed Feb. 28, 2005 for "Floodlight".

Fredric S. Maxik, U.S. Appl. No. 10/915,138, filed Aug. 9, 2004 for "Light Bulb Having Surfaces for Reflecting Light Produced by Electronic Light Generating Sources".

Fredric S. Maxik, U.S. Appl. No. 10/915,278, filed Aug. 9, 2004 for "Lighting Element Using Electronically Activated Light Emitting Elements and Method of Making Same".

Fredric S. Maxik, U.S. Appl. No. 10/915,301, filed Aug. 9, 2004 for "Light Bulb Having Wide Angle Light Dispersion and Method of Making Same".

Fredric S. Maxik, U.S. Appl. No. 10/915,531, filed Aug. 9, 2004 for "Electronic Light Generating Element Light Bulb".

Fredric S. Maxik, U.S. Appl. No. 29/214,892, filed Oct. 8, 2004 for "LED Light Bulb".

Fredric S. Maxik, U.S. Appl. No. 29/214,893, filed Oct. 8, 2004 for "LED Light Bulb".

Fredric S. Maxik and Addy S. Widjaja, U.S. Appl. No. 29/235,139, filed Jul. 27, 2005 for "LED Light Bulb".

Fredric S. Maxik and Addy S. Widjaja, U.S. Appl. No. 29/235,140, filed Jul. 27, 2005 for "LED Light Bulb".

Fredric S. Maxik, U.S. Appl. No. 29/235,514, filed Aug. 2, 2005 for "LED Light Bulb".

Fredric S. Maxik, U.S. Appl. No. 29/254,208, filed Feb. 17, 2006 for "LED Light Bulb".

Fredric S. Maxik, Catherina G.M. Friderici, and Wei Sun, U.S. Appl. No. 29/254,209, filed Feb. 17, 2006 for " LED Light Bulb".

Fredric S. Maxik and Addy S. Widjaja, U.S. Appl. No. 29/254,210, filed Feb. 17, 2006 for "LED Light Bulb".

* cited by examiner

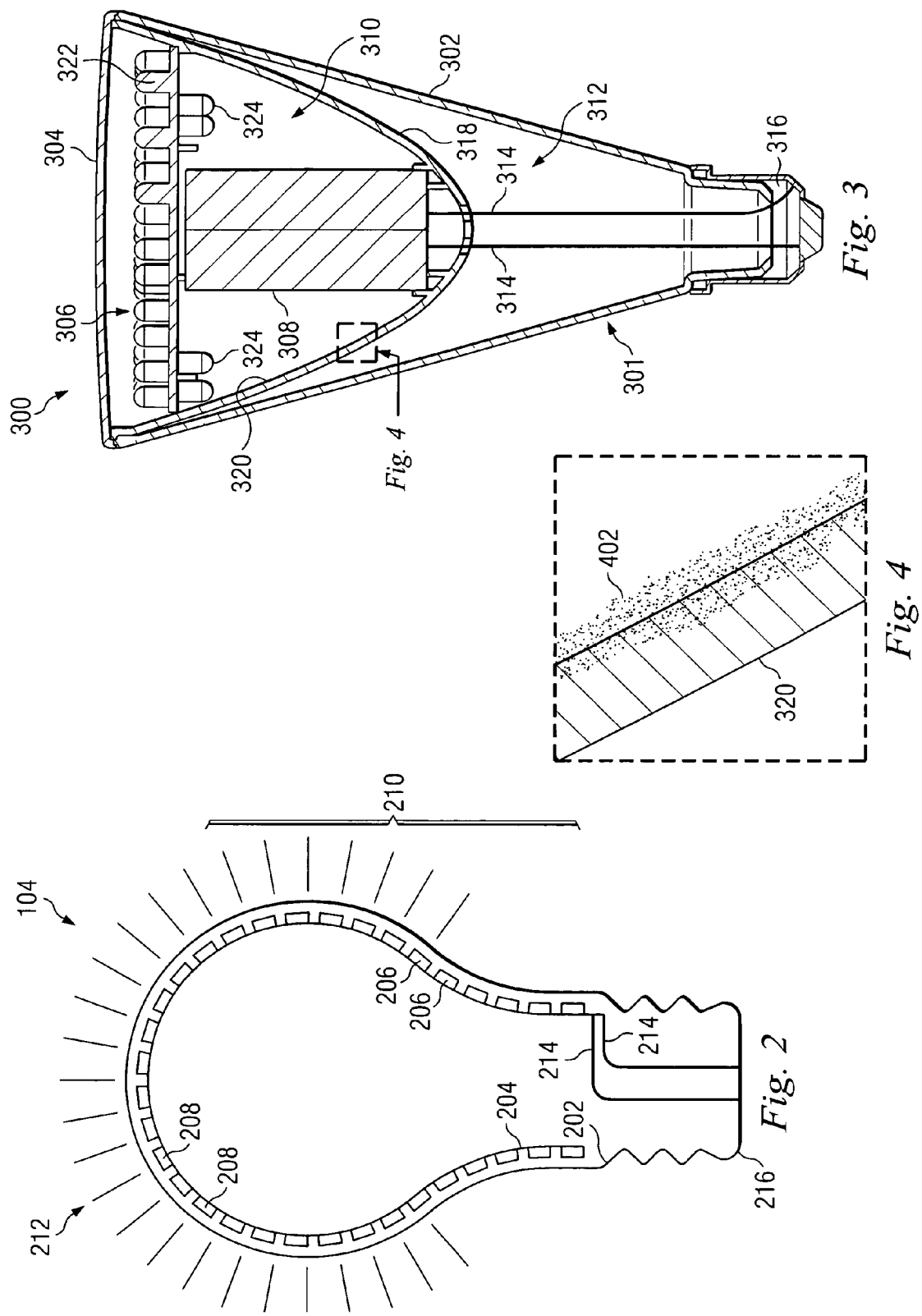

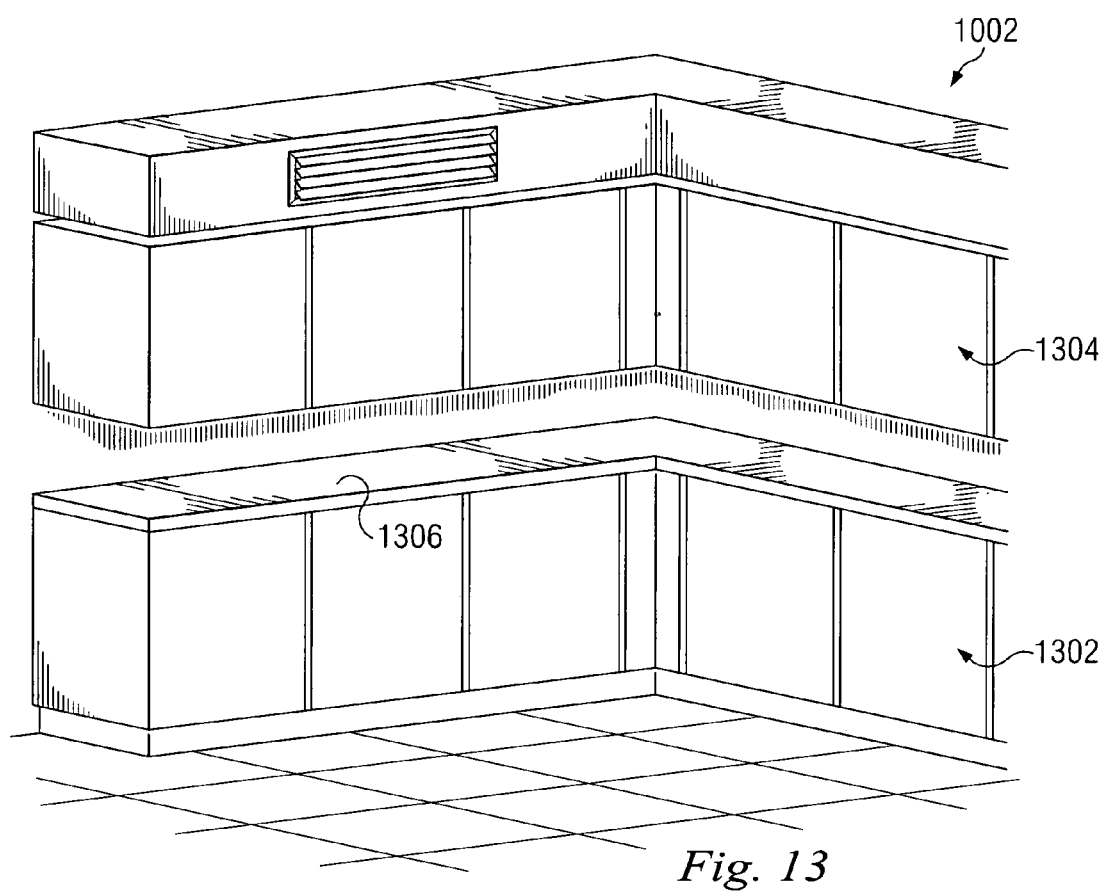
*Fig. 13*
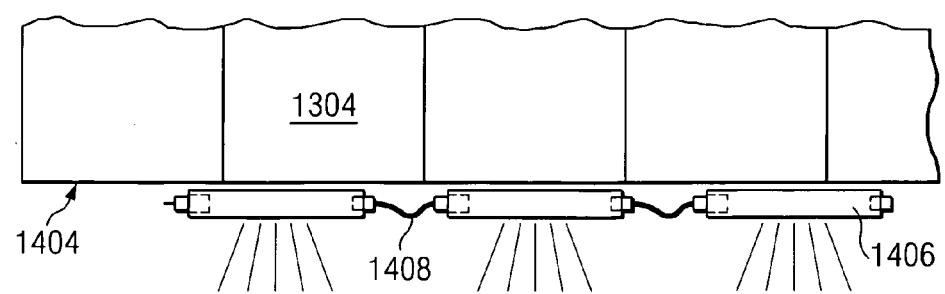
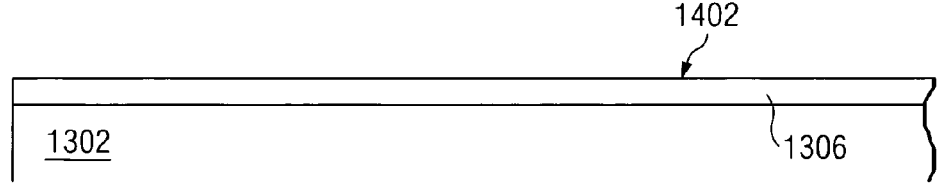
*Fig. 14*

SYSTEM AND METHOD FOR PROVIDING MULTI-FUNCTIONAL LIGHTING USING HIGH-EFFICIENCY LIGHTING ELEMENTS IN AN ENVIRONMENT

CROSS REFERENCE TO RELATED APPLICATIONS

This application is based on U.S. Provisional Application Nos. 60/554,469 entitled Light Element Using Electronically Activated Light Emitting Elements and Method of Making Same filed on Mar. 18, 2004; 60/565,268 entitled Improved electronic Light Generating Element Light Bulb filed on Apr. 23, 2004; 60/567,226 entitled Light Bulb Using Electronic Light Generating Sources filed on Apr. 30, 2004; and 60/567,082 entitled Wide Angle Light Dispersion Electronically Activated Light Bulb and Method of Making Same filed on Apr. 30, 2004. The benefit of the filing date of these Provisional Applications is claimed for this application. The entire contents of these Provisional Applications are incorporated herein by reference.

FIELD OF THE INVENTION

The method relates to multi-functional lighting using high-efficiency lighting elements. More specifically, the invention relates to a method for lighting an environment using single or multi-functional light bulbs comprised of light emitting diodes (LED's) having increased luminescence and light dispersion characteristics.

Problem

Systems for providing programmable lighting environments, such as mood lighting, are known. These lighting systems are focused on providing illumination for an environment using existing conventional lighting elements, such as incandescent, fluorescent, and LED-based lighting elements. These systems provide control of these known conventional lighting elements for a particular room or environment. The control typically consists of turning on and off these conventional lighting elements according to a user's desire and can be programmable.

Some systems employ a computer network that provide illumination and color output commands to individual lighting elements having unique addresses that are capable of receiving these commands and which then provide the requested lighting. These networks can be wireless, and generally include lighting elements which must have transmitters and receivers built into the individual lighting elements for receiving and sending lighting data to and from a central station. Sometimes these lighting elements provide, in addition to lighting, additional purposes or functions, such as sensing. These lighting elements generally require a processor that generates a modulated control signal for controlling the lighting elements.

In other systems, an illumination control signal and a lighting signal are provided together to a decoder where the two signals are split into individual signals. The illumination control signal is then sent to an audio/visual device for providing entertainment and the lighting signal is sent to a lighting source to provide complimentary lighting to the entertainment. These systems require an encoder for encoding the two signals together.

Other attempts to illuminate environments, networked systems including user interfaces, processors, controllers, sensors, LED's and other controllable devices. These systems perform lighting using LED's and conventional lighting devices, such as incandescent lights, fluorescent lights, and the like. The controller controls the lighting arrangements according to a user's desires. However, these systems accordingly require substantial amounts of hardware, wiring, software and the like, which generally translates into higher costs associated with providing these types of lighting systems. Further, since these systems employ conventional lighting devices, the benefits of using low energy LED's is offset by this mixed use of conventional devices.

In addition, the present systems that employ low energy light emitting elements, such as LED's, are limited by the dispersion properties of these LED's, thus, even though a system directs the lights and levels of lights required by a user, the LED's utilized in these systems inherently provide limited light dispersion and functional properties.

However, none of these systems provide multi-functional lighting to an environment utilizing novel multi-functional lighting elements based on a user's desires for the environment. Therefore, there is a need for a system that provides multi-functional lighting to an environment based on a user's desires.

Information relevant to attempts to address these problems can be found in U.S. Pat. No. 6,548,967 issued Apr. 15, 2003 to Dowling, et al.; U.S. Pat. No. 6,211,626 issued Apr. 3, 2001 to Lys, et al.; U.S. Pat. No. 6,166,496 issued Dec. 26, 2000 to Lys, et al.; and U.S. Pat. No. 6,150,774 issued Nov. 21, 2000 to Mueller, et al.; and U.S. Pat. No. 6,608,453 issued Aug. 19, 2003 to Morgan et al. However, each one of these references suffers from one or more of the following disadvantages: high costs, complex installations, lack of functionality, and limited light dispersion properties.

Solution

In accordance with the present multi-functional lighting system, there is a system and method for providing multi-functional lighting that uses high-efficiency lighting elements, such as conventional light emitting diodes (LED's). The system employs high-efficiency lighting elements having varying shapes, sizes, backlighting capabilities, luminescent power, functional characteristics, light dispersion characteristics, and color properties to provide desired lighting environments.

Users are prompted to provide basic information regarding their environments, such the size of the environment and other information such as whether it is indoors, outdoors, functions to be achieved, existing lighting hardware, and the like. The method for lighting then uses this information to determine which light emitting elements to employ for a given environment and the general location for their placement within the environment.

The present method for lighting receives information, such as lighting and functional requirements, regarding a particular environment from a user and then based on this information, determines the required arrangement and types of light emitting elements necessary for providing the desired environment. The present method utilizes light emitting elements having single and multi-functional capabilities to perform a single or multi-functional role within the required arrangement of the desired environment.

Among these functions include: lighting functions, biological impacts functions, pollution control functions (smoke stacks), bacterial control functions, and sterilization functions.

The present method for lighting that uses high-efficiency lighting elements, utilizes high dispersion light emitting elements produced by a combination of highly reflective inner surfaces and backlighting light emitting elements to provide high luminescence and light dispersion. In addition, these light emitting elements utilize optical tuning elements and standoffs to further provide additional dispersion qualities.

It is understood, however, that the present method for lighting could be used with any of a variety of light sources and, particularly, light sources which are electronically activated or generated. As an example, in recent years there have been proposals to produce light sources using various known inorganic materials and, for that matter, some organic materials. Thus, the present invention is applicable with each of these light generating elements which are all electronically energized or operated. For purposes of the present application, however, the invention will be described in terms of light emitting diodes as the light generating elements, since they are the preferred form. However, it is to be understood that the invention is not so limited.

This present method for lighting thereby provides a unique and novel input arrangement for a user to provide basic information related to their environment in addition to their desires for the environment to be provided by the present lighting system. The present method for lighting then takes this information and determines the types of novel light emitting elements to employ and their locations for placement within the environment to provide the desired environment.

The present multi-functional lighting system for providing a desired function in an environment using high-efficiency lighting elements. The high-efficiency lighting elements are selected for producing a desired function. An optical tuning element is substantially disposed over the high-efficiency lighting elements for providing high-efficiency lighting. In addition, the present multi-functional lighting system determines the best location for the high-efficiency lighting elements located within the environment. The high-efficiency lighting system calculates an area of a portion of the environment for determining the quantity of at least one high-efficiency lighting elements to provide the desired function for the portion of the environment.

The present multi-functional lighting system further provides for adjusting the angle of dispersion of light emitted from the high-efficiency lighting elements and shaping the light emitted from the high-efficiency lighting elements. The present multi-functional lighting system also provides for adjusting the output of the one high-efficiency lighting elements. Preferably the high-efficiency lighting elements are light emitting diodes that emit light in the visible and invisible wavelength range. The functions that these high-efficiency lighting elements provide includes lighting, bacteriological control, biological control, pest control, and pollution control.

In one aspect of the system, the system further selects among at least two different of the light emitting diodes of said high-efficiency lighting element for providing said function in said environment. Preferably, the high-efficiency lighting elements include circuitry for supplying a peak current above the maximum forward current rating of the high-efficiency lighting element, when energized.

However, it should be understood that the accompanying drawings and this detailed description are set forth only for purposes of illustrating the general principles of the invention.

BRIEF DESCRIPTION OF THE DRAWINGS

FIG. 2 illustrates a cross-section view of an interior of a light bulb with a flexible formed substrate disposed therein and having a plurality of light emitting elements mounted thereon;

FIG. 3 illustrates a cross-section view of another embodiment of a light bulb having wide angle dispersion material incorporated therein;

FIG. 4 illustrates an expanded cross-section of a side wall of the light bulb of FIG. 3 depicting crystalline particulate material incorporated into the housing of the light bulb;

FIG. 13 illustrates a perspective view of an area in a room where multi-functional lights are employed;

FIG. 14 illustrates a side elevation view of the area depicted in FIG. 13 where multi-functional lights are employed;

DETAILED DESCRIPTION OF THE DRAWINGS

Figure 1:
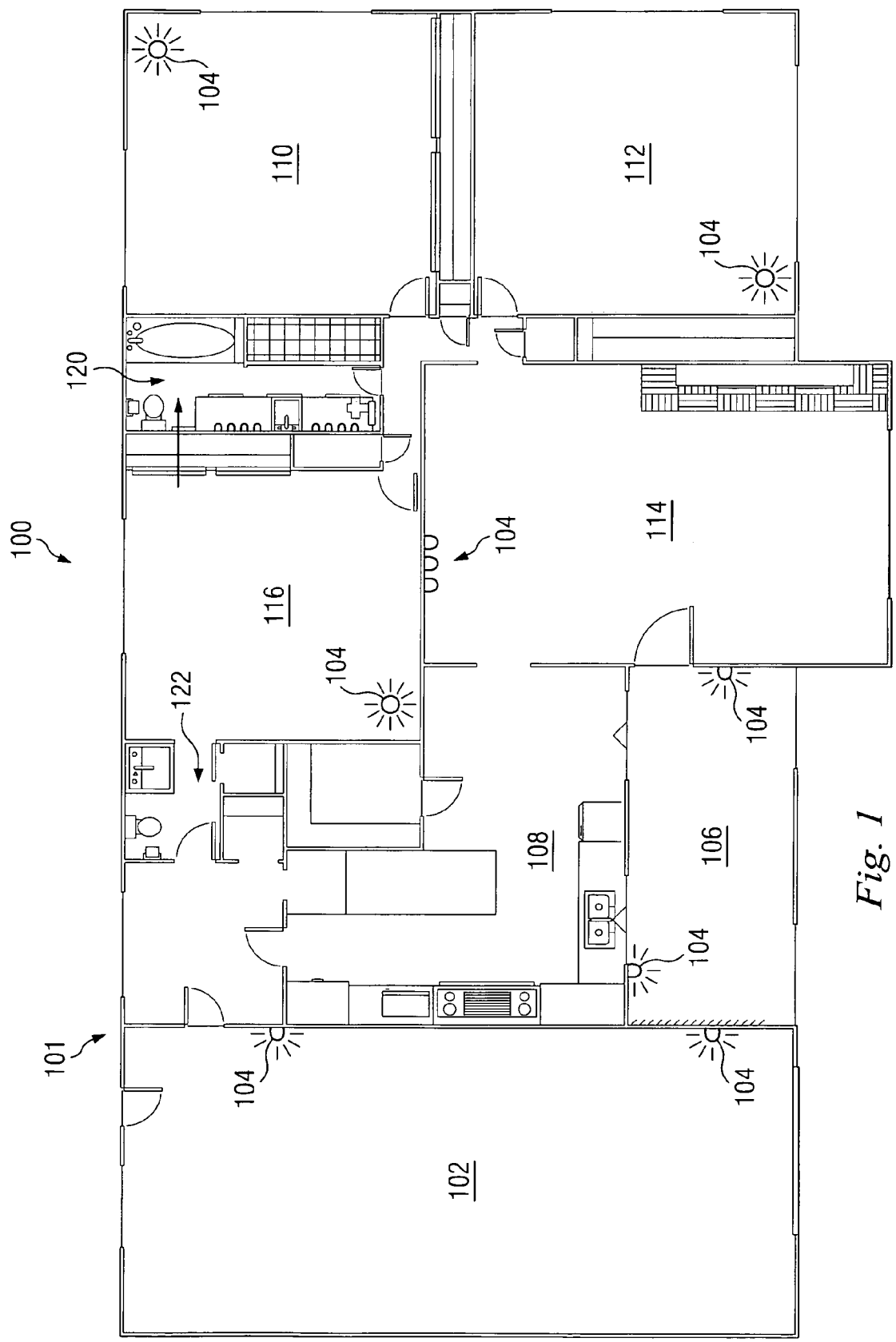
FIG. 1 illustrates a top elevation view of the present multi-functional lighting system in an exemplary environment.

FIG. 1 illustrates an embodiment 100 of an exemplary environment 101 of the present multi-functional lighting system. The environment 101 depicted in FIG. 1 is a house, however, the present multi-functional lighting system 100 can be employed in any other environment where multi-functional lighting may be provided, such as office building, airports, warehouses, and other commercial and residential environments. Environment 101 includes a garage 102 and light bulbs 104 attached to the wall of the garage 102, a patio 106 including light bulbs 104 attached to the exterior walls of the patio 106, and a kitchen 108 having light bulbs incorporated into the ceiling (300 in FIG. 12). Environment 101 further includes bedrooms 110, 112, and 116, and a family room 114, each of these rooms having light bulbs 104 located therein. Bathrooms 120 and 122 are also depicted in environment 101.

FIG. 2 illustrates an exemplary light bulb 104 of the present multi-functional lighting system 100. Light bulb 104 comprises a housing 202 with a base 216 connected thereto. The housing 202 can be in the form of a standard incandescent light bulb housing, or any other desirable form or shape. The base 216 normally adopts the form of a conventional Edison base, although any base could be used. The housing 202 of the light bulb 104 is transparent or at least light translucent. Light is provided by a plurality of light emitting elements 206 and 208 that are connected to a formed substrate 204 that contours to the form of the inside wall of the housing 202. In one aspect of the present multi-functional lighting system 100, light emitting elements 206 emit light substantially in the visible wavelength range and light emitting elements emit light substantially in the non-visible wavelength range. The light ray traces 212 depict the visible wavelength light and the light ray traces 210 depict the non-visibly wavelength light emitted from the light bulb 104. Preferably, the light emitting elements 206 and 208 are light emitting diodes. The functions of these light emitting elements 206 and 208 are describe more fully below. In addition, the locations and number of the light emitting elements 206 and 208 located on the formed substrate 204 varies in accordance with the desired operation and function of the light bulb 104.

The formed substrate 204 may be held in place within the housing by a support (not shown) which can be connect to the base 216 or elsewhere on the housing 202 to provide support for the formed substrate 204. Electrical power is provided to the light emitting elements 206 and 208 via electrical connectors 214 which connect to each light emitting element 206 and 208 and to the base 216. Control circuitry (not shown) is generally interposed between said base 216 and said light emitting elements 206 and 208 and can be located substantially in the base 216, or elsewhere such as on the underside of the formed substrate 204. Electricity supplied to these electrical connectors 214 can be AC or DC, in the case of AC the necessary control circuitry may be located for converting the AC power to DC power is used. This control circuitry may include resistors, rectifying diodes, and Zener diodes. Rectifying diodes convert AC to DC, should the power source to the LED's be AC. Rectifying diodes are not needed when the power supply is DC. Control circuitry further includes the necessary circuitry for operating sensors and the like as described herein. Though the housing 202 for light bulb 104 is depicted as having a conventional shape or form, the present multi-functional lighting system 100 includes light bulbs having any desirable shape or form to suit a particular application and still be within the inventive concepts disclosed herein. For example, as will be discussed below, the shape of light bulb 104 and 300 can have a tubular shape or other otherwise non-conventional shape as needed for the application of the present multi-functional lighting system 100.

FIG. 3 illustrate another embodiment 300 of a light bulb including a housing 301 having a somewhat conically shaped side wall 302 and which is provided at one end with a base 316 such as a conventional Edison base and which is provided at the other end with a transparent or translucent end cap 304. The base 316 is of the type which is used in a conventional incandescent light socket or other conventional lighting fixture socket, such as used in fluorescent lighting fixtures and the like.

A cavity 312 is defined by the area between the side wall 302 and the transparent or translucent end cap 304. Mounted within the cavity 312 of the housing 301 is a support 308 for supporting a substrate 322 having a plurality of light emitting elements 306. The entire support 308 and light emitting elements 306 are covered partially or fully by the end cap 304. The substrate 322 is preferably transparent and may adopt the form of a printed circuit board.

In this embodiment, a semi-hemispherical shaped insert 318 having an inside surface 320 is inserted into the cavity 312 to provide a base for the support 308 and the inside surface 320 for reflecting light that enters a cavity 310 of the insert 318. The cavity 310 is defined by the area between the insert 318 and the end cap 304.

Attached to the surface facing the end cap 304 of the substrate 322 are the plurality of light emitting elements 306 as described above. These light emitting elements 306 emit light toward the end cap 304. In addition to these light emitting elements 306, are optional light emitting elements 324 connected to the other surface of the substrate 322. These light emitting elements 322 emit light substantially toward the inside wall 320 of the insert 318.

Referring to FIG. 4 is an expanded view of a portion of the insert 318 depicting a crystalline particulate material 402 incorporated into the inside surface 320. As can be seen from FIG. 4, the crystalline particulate material 402 is incorporated on the inside surface 320 of the insert 318 and also within the material comprising the insert. The crystalline particulate material 402 is employed to reflect light entering the cavity 310 back outward through the substrate 322 for providing improved light dispersion properties. This backlighting improves the light dispersion qualities of the light bulb 300.

In addition, electrical connectors 314 can be routed through the support 308 or through or along the side walls 302 of the housing 301. Electricity supplied to these electrical connectors 308 can be AC or DC, in the case of AC the necessary circuitry (not shown) may be located in the base 316 for converting the AC power to DC power. This circuitry may include resistors, rectifying diodes, and Zener diodes. Rectifying diodes convert AC to DC, should the power source to the LED's be AC. Rectifying diodes are not needed when the power supply is DC. In another aspect of the present light bulb, the circuitry may be located elsewhere, such as in the support 308 and be covered with a cover plate (not shown) if desired, which may be transparent in construction. Preferably, the light emitting elements 306 and 324 are light emitting diodes.

Figure 5:
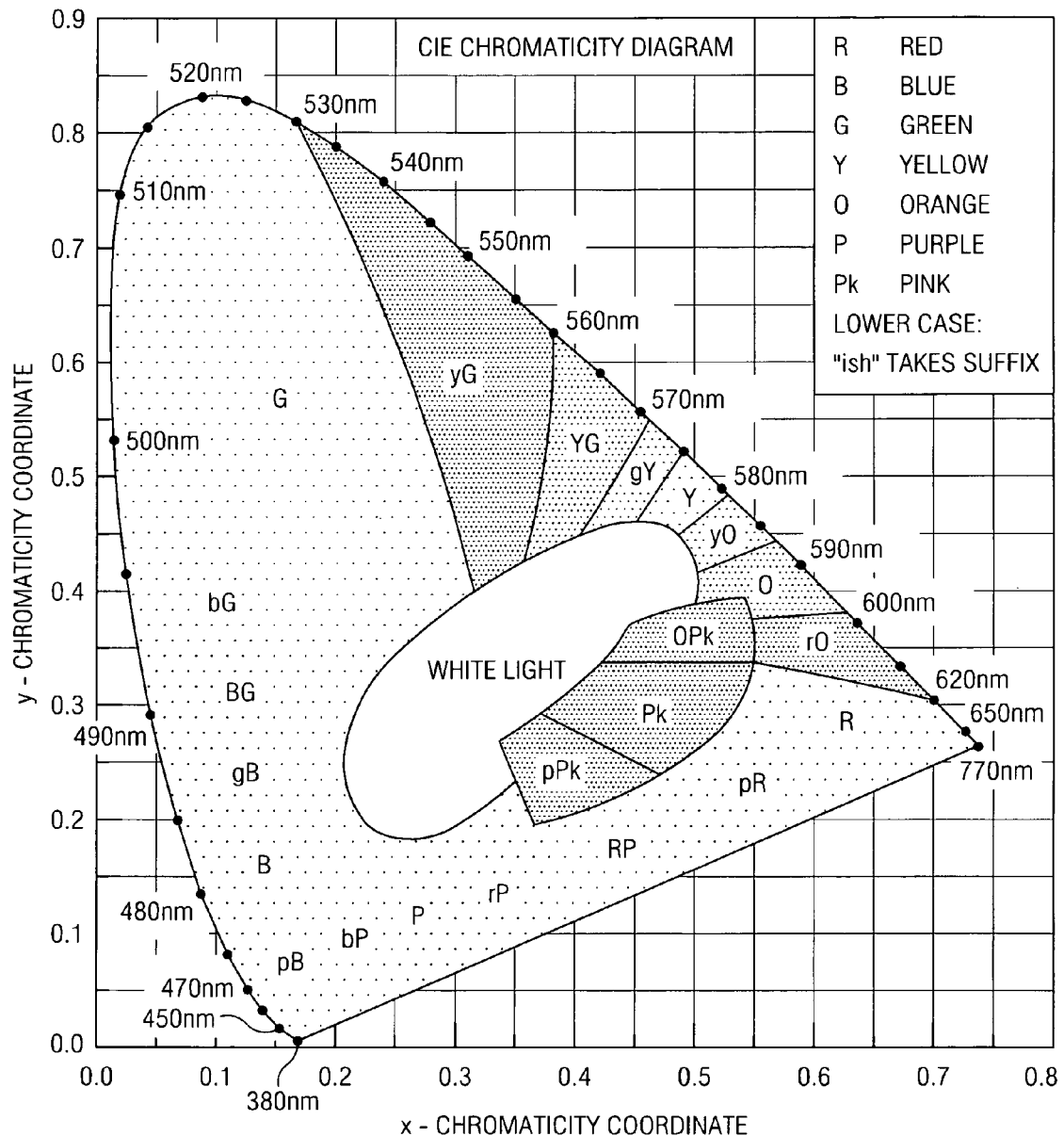
FIG. 5 illustrates a Commission Internationale de L'Eclairage (CIE) chromaticity chart.

FIG. 5 illustrates a Commission Internationale de L'Eclairage (CIE) chromaticity chart, which the present multi-functional lighting system 100 preferably employs for determining the colors of the light emitting elements 206, 208, 306, and 324 for providing the multi-functional aspects herein described. Wavelengths within the visible range extend from red (approximately 760-645 nm) through orange, yellow, green and blue, to violet (approximately 425-380 nm). The "purity" of a light is a measurement of the degree to which "colored" light departs from truly monochromatic light (light of a single wavelength only) and approaches white light, which consists of a mixture of all spectral wavelengths, such as when red, green, and blue lights are mixed together to produce a white light. The individual colored lights—red, green, and blue—are mixed under the end cap 304 or the housing 202 of the light bulbs 300 and 104, respectively, to provide white light. The CIE has established an internationally agreed system of objective color notation, wherein the monochromatic primary wavelength are 700.0 nm for red, 546.1 nm for green, and 435.8 nm for blue. The light bulbs 104 and 300 can also produce other colors than white light, in which case, the emitting elements 206, 208, 306, and 324 are selected using the CIE diagram to provide the desired color. For example, if an emerald green color is desired, then the light emitting elements 206, 208, 306, and 324 are selected by the co-ordinates x equals 0.210 and y equals 0.710. Preferably, the light emitting elements 206, 208, 306, and 324 are light emitting diodes (LEDs), so to produce the emerald green color, a mix of red, green, and blue LEDs are selected to produce the emerald green color.

Additionally, LEDs emit light in the non-visible wavelength range, such as the ultraviolet (UV) wavelength range. In one aspect, the light bulbs 104 and 300 emit non-visible wavelength light in the UV range. In the case where the light emitting elements 206, 208, 306, and 324 are LEDs, the desired wavelength of non-visible light is produced by selecting the proper mixture of LEDs to produce the desired non-visible wavelength light. The non-visible wavelength light adds further functionality to the light bulbs 104 and 300 of the present multi-functional lighting system 100. Gallium nitride LEDs are known and emit light in the UV wavelength range of 275-395 nm.

By way of illustration, if a 3,700 Kelvin color is desired, the mix of the light emitting elements 206, 208, 306, and 324 would be 50 red, 27 green, and 23 blue to achieve this color. In this aspect, designed housing 202 and end cap 304 incorporate the proper micro optics, such as finishes or thin films, mixes the color to provide the desired end product. The number, arrangement, and color selection of the light emitting elements 206, 208, 306, and 324 on the formed substrate 204 creates a flexible light bulb 104 that can meet the desired lighting requirements of a given situation.

Figure 6:
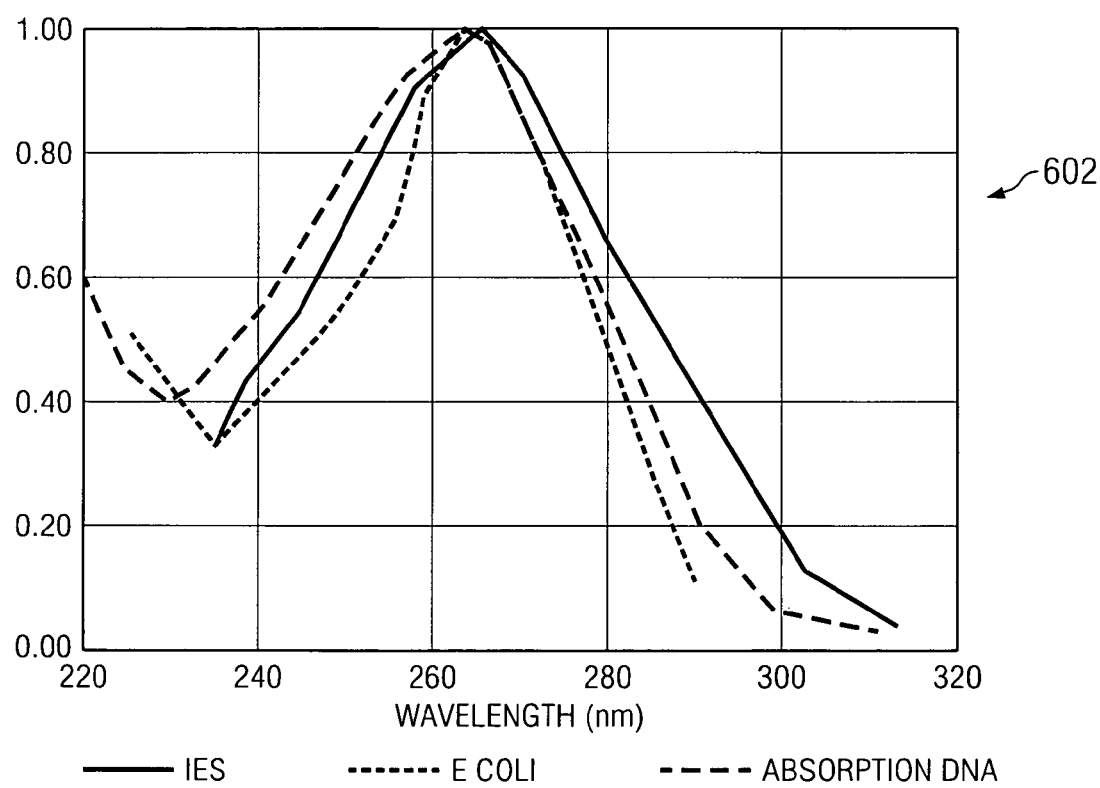
FIG. 6 illustrates a germicidal action spectrum chart the depicts the ultraviolet light (radiation) wavelength that is most effective at destroying microorganisms.

When desired, the light bulbs 104 and 300 provide multi-functions, in addition to lighting the environment 101. In one aspect of the present multi-functional lighting system 100, a portion or the entire light bulb 104 and 300 emits non-visible wavelength light to provide germicidal disinfection sterilization of surfaces. In this aspect, the non-visible wavelength light emitted from the light bulbs 104 and 300 act as a germicidal disinfectant destroying living microorganisms. Referring to FIG. 6, a germicidal disinfection sterilization chart 602 is illustrated. As can be seen from chart 602, non-visible wavelength light emitted in the range of between 240 nm-280 nm, will destroy approximately from 60%-100% most of the microorganisms it comes in contact with, including *Escherichia coli*. Similar wavelengths of non-visible UV light are also used for germicidal sterilization in air, thus, in one aspect of the present multi-functional lighting system 100, the light bulbs 104 and 300 include light emitting elements 206, 208, 306, and 324 that emit UV wavelength in the 240 nm-280 nm for air purification. Additional commonly known functions of UV wavelength light may be employed with the light bulbs 104 and 300 to suit the design of the present multi-functional lighting system 100.

In addition, the functionality of the light bulbs 104 and 300 is further increased by the use of non-visible wavelength light emitting elements 206, 208, 306, and 324 that provide additional functionality. For example, it is known that insects and bugs are attracted to light in the wavelength range at or below 490 nm, so light bulbs 104 and 300 are provided with light emitting elements 206, 208, 306, and 324, preferably light emitting diodes, that do not emit light at or below 490 nm, thus keeping bugs away from areas where the light bulbs 104 and 300 are employed.

Figure 7:
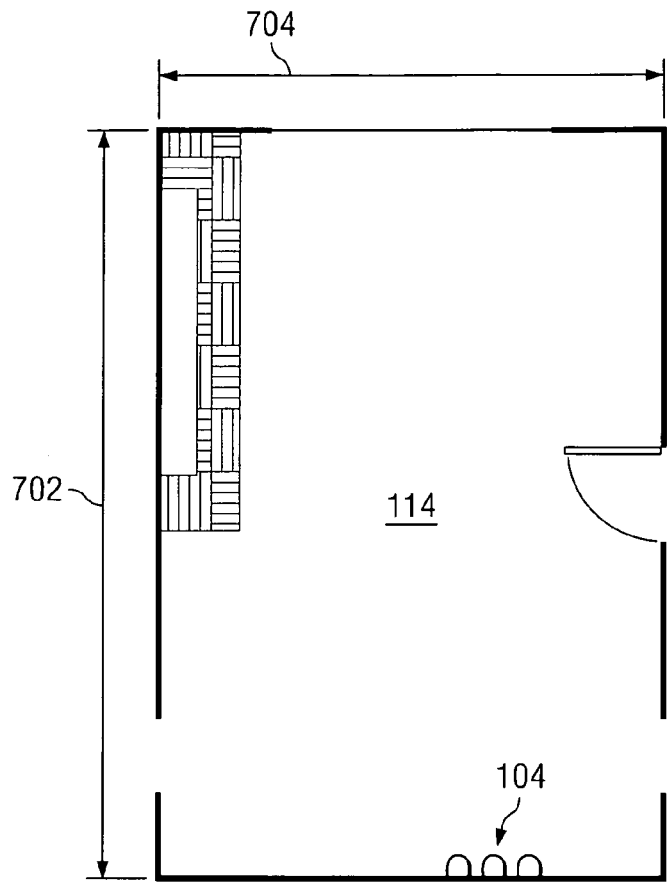
FIG. 7 illustrates a top elevation view of a room in the exemplary environment depicting dimensional lines for determining the area of the room.
Figure 8:
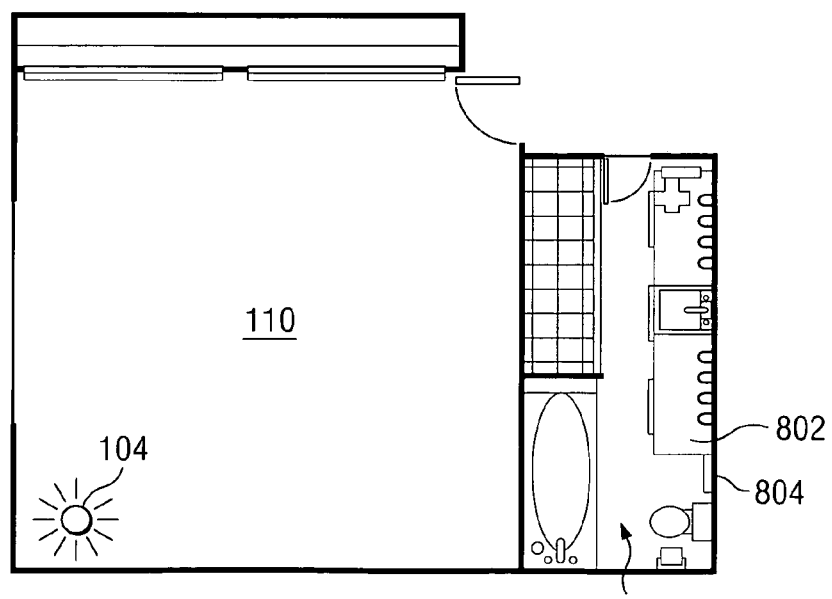
FIG. 8 illustrates a top elevation view of another room in the exemplary environment depicting areas of the room where multi-functional lights are employed.
Figure 9:
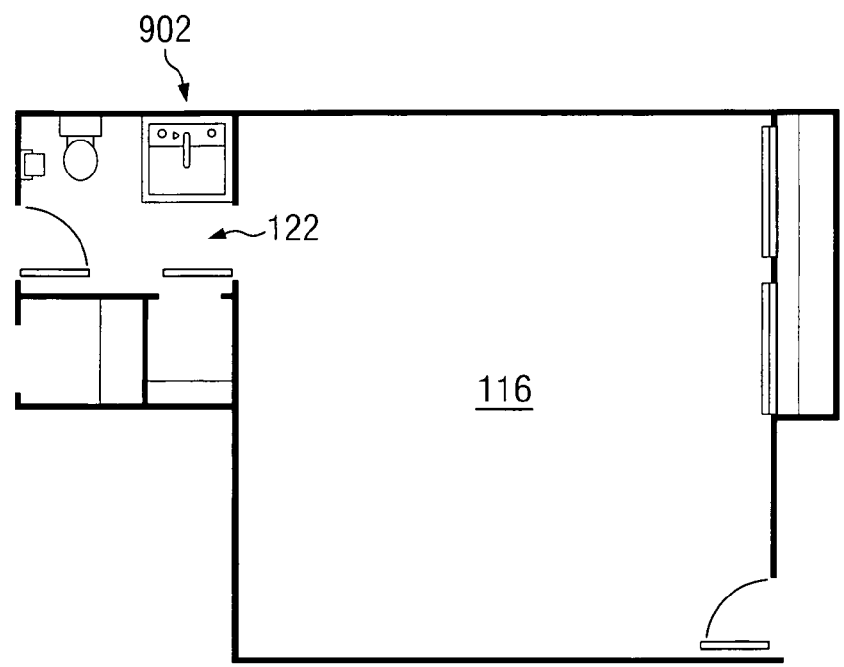
FIG. 9 illustrates a top elevation view of another room in the exemplary environment depicting areas of the room where multi-functional lights are employed.
Figure 10:
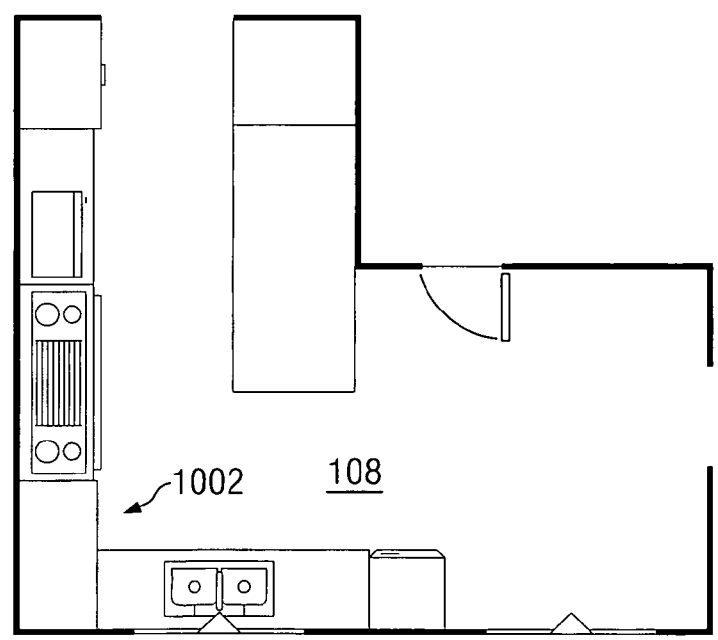
FIG. 10 illustrates a top elevation view of another room in the exemplary environment depicting areas of the room where multi-functional lights are employed.

FIG. 7 illustrates the family room 114 of the environment 101 depicting light bulbs 104 located on the wall being used as down lighting. In one aspect of the present multi-functional lighting system 100, room dimensions 702 and 704 may be entered into the multi-functional lighting system 100 for determining the number and type of light bulbs 104 and 300 to be provided or used within the family room 114. FIG. 8, illustrates the bedroom 110 and bathroom 120 of the environment 101. In one aspect of the present multi-functional lighting system 100, bathroom 120 depicts locations 802 and 804 within the bathroom 120 where bacterial sterilization provided by the light bulbs 104 preferably occurs. FIG. 9 illustrate another bedroom 116 depicting another location 902 within bathroom 122 where bacterial sterilization provided by light bulbs 104 also preferably occurs. FIG. 10 illustrate the kitchen 108 of the environment 101 depicting yet another location 1002 where bacterial sterilization provided by the light bulbs 104 occurs.

Figure 11:
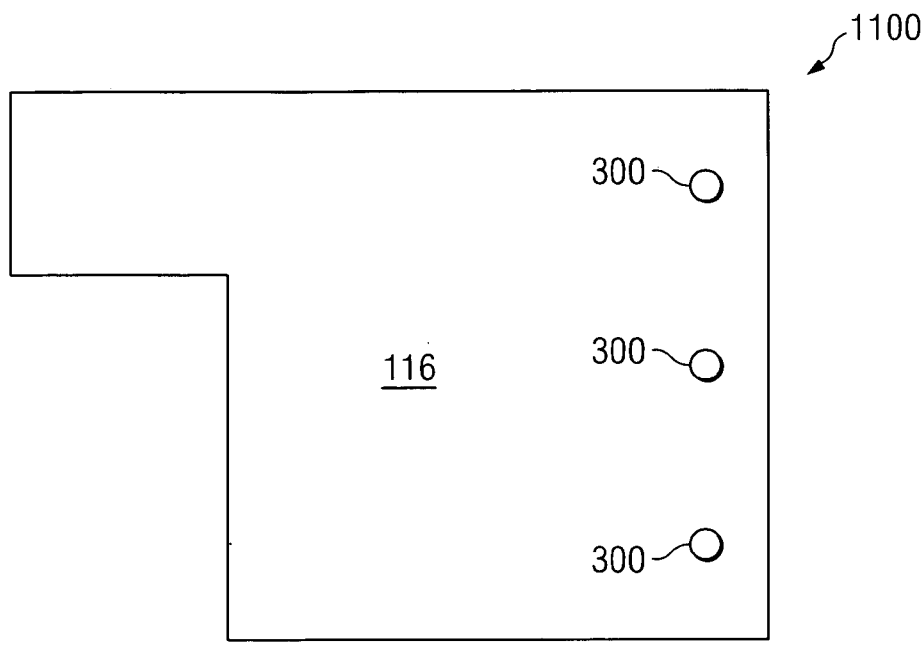
FIG. 11 illustrates a bottom elevation view of the ceiling of the room in FIG. 9 depicting flood-type lights located in the ceiling.
Figure 12:
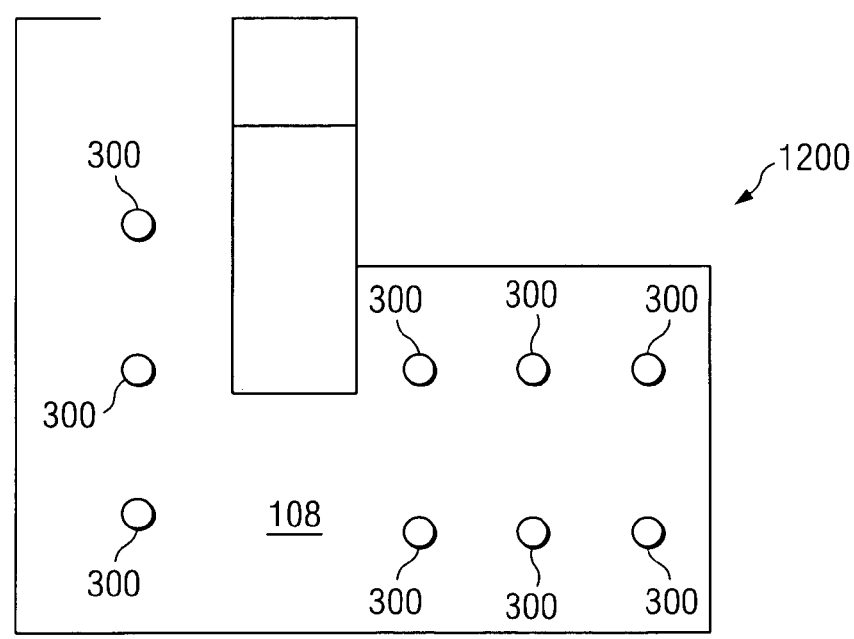
FIG. 12 illustrates a bottom elevation view of the ceiling of the room in FIG. 10 depicting flood-type lights located in the ceiling.

FIGS. 11 and 12 illustrates the ceilings 1100 and 1200 of bedroom 116 and kitchen 108, respectively, depicting flood type light bulbs 300 arranged in the ceiling for providing light into the rooms. In another aspect of the environment 101, these flood-type light bulbs 300 may be used in other rooms of the environment, though not presently depicted.

FIG. 13 illustrates the location 1002 in the kitchen 108 where bacterial sterilization, in one aspect, may occur. In FIG. 13, a countertop 1306 is located between a set of upper cabinets 1304 and lower cabinets 1302. FIG. 14 illustrates the upper cabinets 1304 and a set of light bulbs 1406 having a tubular shape and components and elements similar to those described herein with respect to light bulbs 104 or 300. Electrical connections 1408 provide electricity from an outlet (not shown) to the light bulbs 1406. Light emitting from light bulbs 1406 reaches countertop surface 1402 of countertop 1306 to provide lighting and bacterial sterilization, as described herein, for the countertop surface 1402. In one aspect, the light emitting elements 206, 208, 306, and 324 contained within the light bulbs 1406 are light emitting diodes. Additionally, the light emitting diodes 206, 208, 306, and 324 are arranged such that those that emit UV wavelength for the function of bacteriological or germicidal sterilization, emit the light downward directly towards the countertop surface 1402.

Figure 15:
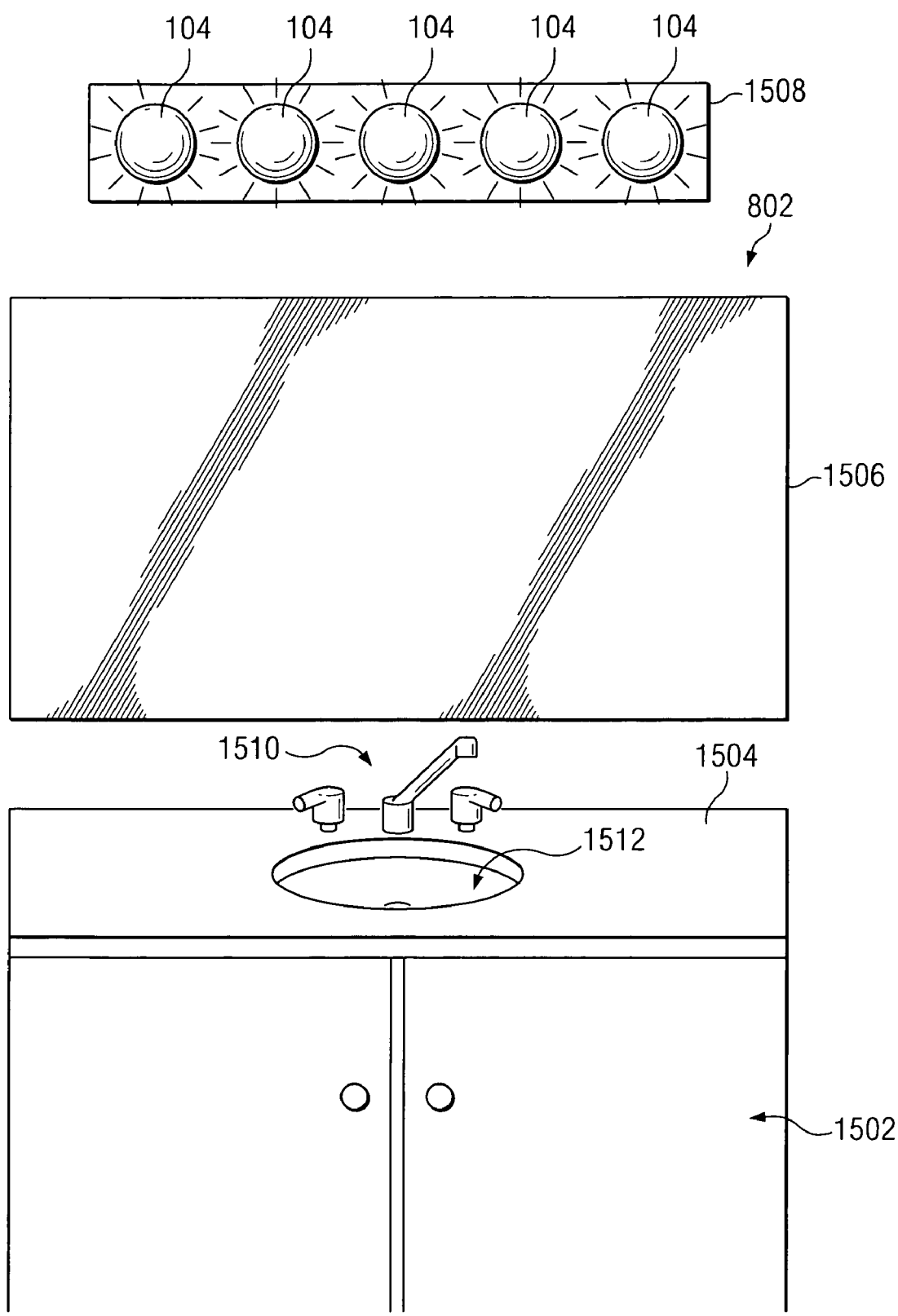
FIG. 15 illustrates a perspective view of an area in the room depicted in FIG. 8 where multifunctional lights are employed.

FIG. 15 illustrates location 802 of bathroom 120 where light bulbs 104 are used for the purpose of lighting the bathroom and sterilizing surfaces within the bathroom 120. A cabinet 1502 includes a cabinet surface 1504, sink 1512, and fixtures 1510. In addition, a mirror 1506 is located above the cabinet 1502. The light bulbs 104 are attached to a light bulb bar or mounting 1508 and are arranged such that portions of the light bulbs 104 that emit non-visible UV wavelength light face the cabinet surface 1504. In one aspect, the light emitting elements 206, 208, 306, and 324 contained within the light bulbs 1406 are light emitting diodes. Additionally, the light emitting diodes 206, 208, 306, and 324 are arranged such that those that emit UV wavelength for the function of bacteriological or germicidal sterilization, emit the light downward directly towards the cabinet surface 1504.

Figure 16:
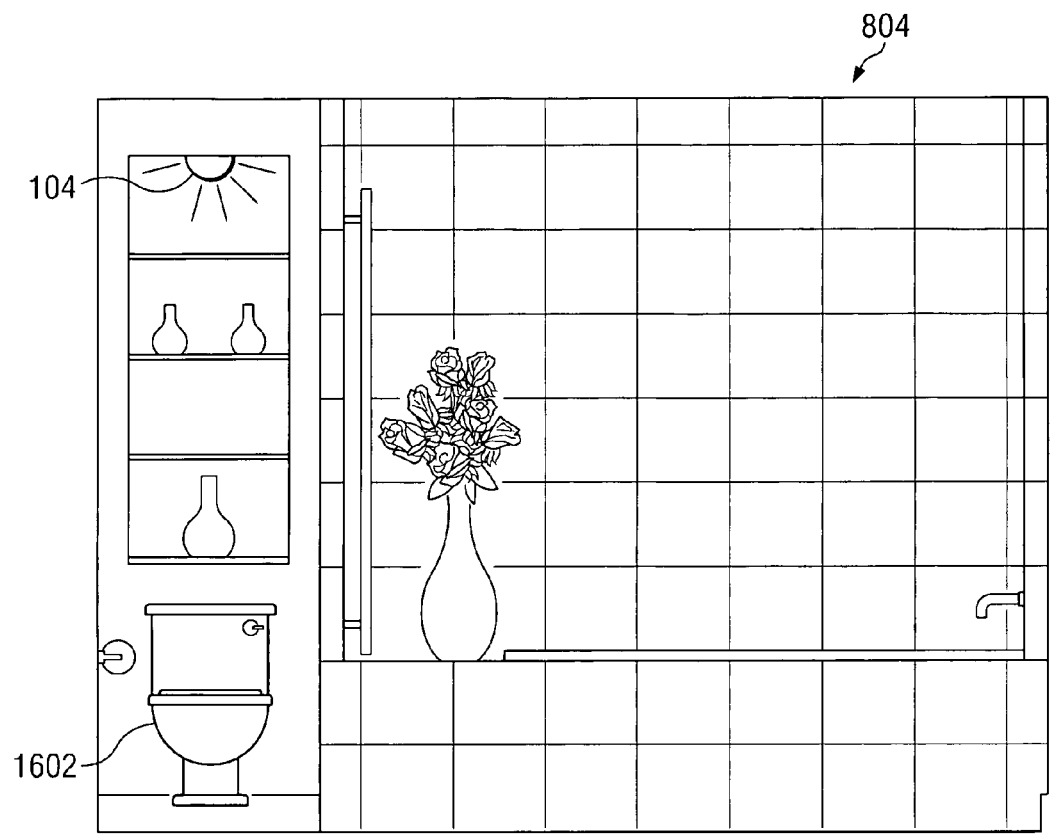
FIG. 16 illustrates a perspective view of another area in the room depicted in FIG. 8 where multifunctional lights are employed.

FIG. 16 illustrates location 804 of bathroom 120 where a light bulb 104 is located for downlighting the toilet 1602. As described above, the light bulb 104 may provide both lighting for the room and also bacterial and germicidal sterilization to the surfaces of the toilet 1602. In one aspect, the light emitting elements 206, 208, 306, and 324 contained within the light bulbs 1406 are light emitting diodes. Additionally, the light emitting diodes 206, 208, 306, and 324 are arranged such that those that emit UV wavelength for the function of bacteriological or germicidal sterilization, emit the light downward directly towards the toilet 1602 or other surfaces were it would be desirable to have bacterial or germicidal sterilization.

Additionally, in one aspect of the present multi-functional lighting system, those light emitting elements 206, 208, 306, and 324 that provide the function of bacterial or germicidal control are on a timer or other initiation means for activation of the UV wavelength for sterilizing the countertop surface 1402, cabinet surface 1504, sink 1512, fixtures 1510, and toilet 1602 during the night when occupants are sleeping. Lighting functions may be operable during the entire day and may or may not be on a timer.

Figure 17:
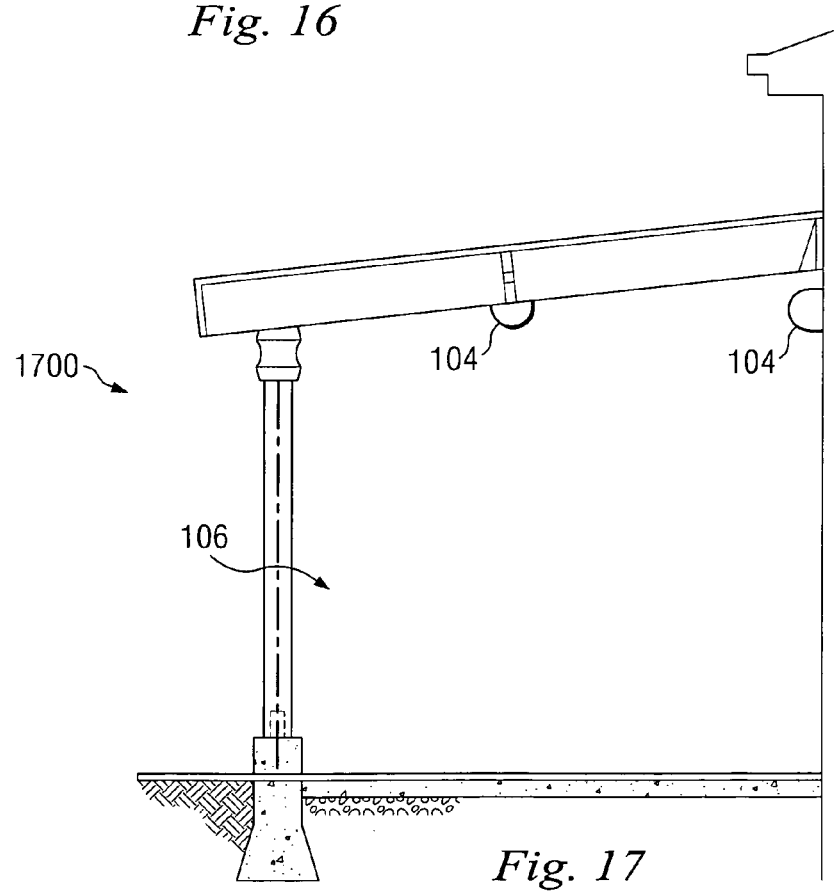
FIG. 17 illustrates a side elevation view of another area in the exemplary environment where multifunctional lights are employed.

FIG. 17 illustrates patio 106 having a covering 1700 for providing shelter. In one aspect, light bulbs 104 are arranged to provide lighting and bug or insect deterrence or control. In this example, the light emitting elements 206, 208, 306, and 324 are preferably light emitting diodes and emit light in the visible wavelength for providing light but without producing any light having a wavelength of 490 nm or less.

In one aspect of the present multi-functional lighting system, housing 202 and end cap 304 may comprise different shapes, forms, thicknesses, patterns, and etchings to provide further dispersion of the light from the light bulbs 104 and 300.

The housing 202 and end cap 304 can be manufactured to generally any desired form. The housing material can be any material suitable for the purposes of molding or forming the housing 202 and end cap 304 to the desired forms, such as round or half forms, donut forms, and forms of present day neon lighting. The housing 202 and end cap is made from a moldable material that is transparent, semi-transparent, and/or translucent. Such materials may include polymers, copolymers, or other moldable materials, such as polycarbonates, plastics, or the like. In addition, the housing 202 or portions of the housing 202 and end cap 304 can be manufactured with a certain form, shape, pattern, or the like to change the light dispersion pattern emitted from the light emitting elements 206, 208, 306, and 324. For example, during the manufacturing of the housing 202 and end cap 304, a specific die or tool to shape or form the housing 202 and end cap 304 in a particular way to tune the light passing through the housing 202 and end cap 304. These dies or tools effect the imprint, shape, or form of the housing 202 and end cap 304 or the surface, internally or externally, of the housing 202 and end cap 304. In addition, an optional thin film (not shown) can be applied to the housing 202 or end cap to further tune the optical light emitting from the light bulbs 104 and 300. In addition, the thin film or finish may be created on the housing 202 or end cap 304 to provide tune the light dispersion pattern provided by the light bulbs 104 and 300. The thin film can also be applied to the housing 202 and end cap 304 for further tuning a different light dispersion pattern from the light bulbs 104 and 300. In another aspect of the present lighting element, a pattern is etched, scratched, or polished in the housing 202 and end cap 304 to tune yet another light dispersion pattern from the light bulb 104 and 300. In yet another aspect of the present lighting element, a grit pattern is included in the mold for the housing 202 and end cap 304 to provide a further micro optic pattern in the finished lens portion of the housing 202 and end cap 304 when molding the light bulbs 104 and 300 to further tune the light emitting from the light bulbs 104 and 300. The housing 202 and end cap 304 can be molded as one piece or several pieces and later assembled together using an adhesive or other fixture means.

Figure 18:
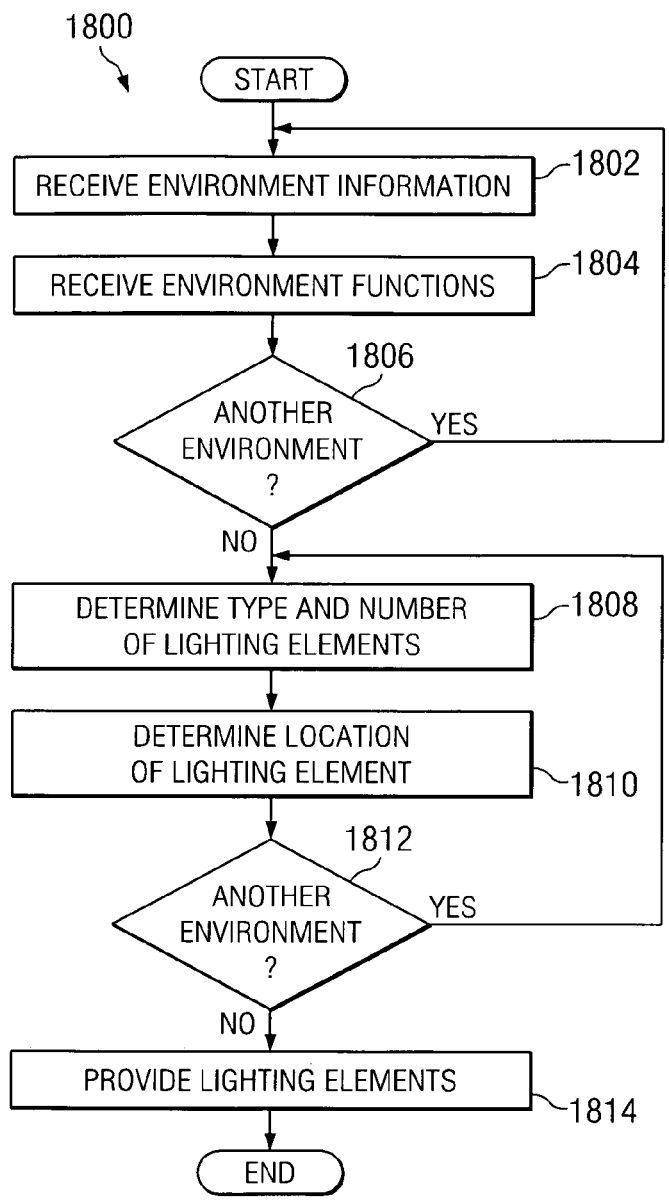
FIG. 18 illustrates in block flow diagram form a process for providing the present multi-functional lighting system in an exemplary environment.

The present multi-functional lighting system further provides a method 1800 for determining the required types and number of light bulbs 104 and 300 to be used in a system based on basic information provided by user related to a particular environment 101. FIG. 18 illustrates a block flow diagram of an exemplary method 1800 in accordance with the present multi-functional lighting system 100.

In step 1802, a user inputs information into the multi-functional lighting system 100 related to a particular environment 101. This input can be via a telephone conversation, via a written conventional form that the user completes, via the internet through a web based e-commerce site, or other shapes or forms of data transmission. Further, the present multi-functional lighting system may prompt the user through each of the below noted steps via the same means for data transmission as just described. Step 1804 further prompts or request the user to provide information related to the desired functions of a particular environment that the user wishes to exist. Step 1806 continues requesting information from the user until the user has provided all of the information they wish to enter into the present multi-functional lighting system 100.

In step 1808, the present multi-functional lighting system 100 determines the type of lighting elements 206, 208, 306, and 324 and light bulbs 104 and 300 to employ in the environment 101 based on the information provided by the user. In step 1810, locations of the selected light bulbs 104 and 300 are determined again, based on the information provided by the user. Step 1812 continues the process until all environments 101 and their corresponding multi-functional lighting requirements have been determined or addressed. In step 1814, the selected light bulbs 104 and 300 are provided to the user.

Figure 19:
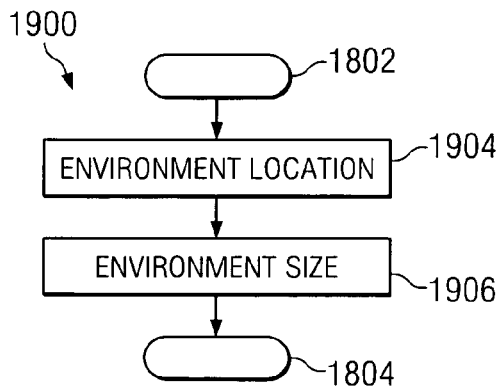
FIG. 19 illustrates in block flow diagram form a process for providing environmental information related to an exemplary environment.

FIG. 19 illustrates a further method 1900 related to step 1802 for providing the information by the user related to a particular environment 101. In step 1904, the user inputs information related to a particular location, such as a room, like bathroom 120. Since germicidal and bacterial sterilization may be desired in bathroom 120, the present multi-functional lighting system 100 uses this information when determining the types of light bulbs 104 and 300 and the light emitting elements 206, 208, 306, and 324 contained within those light bulbs 104 and 300. In addition, step 1906 accepts input or information regarding the size of the particular room to determining the spacing and number of light bulbs 104 and 300 required by the room.

Figure 20:
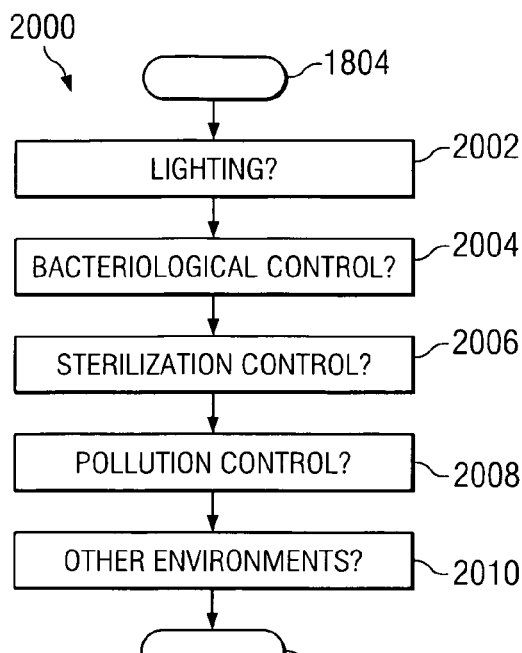
FIG. 20 illustrates in block flow diagram form a process for providing environmental function information related to an exemplary environment.

FIG. 20 illustrates a further method 2000 related to step 1804 for providing the information by the user related to a particular function desired by the user for the environment 101. In step 2002, the user inputs or enters information regarding the type of lighting that the user is desiring to be in a particular room of the environment 101. For example, the user might wish to have downlighting for a painting or similar exhibit as illustrated in FIG. 7. In step 2004, if any bacterial, viral, or germicidal control is desired by the user, then this information is inputted as well. In step 2006, additional sterilization controls known are entered according to the user's desires. In step 2008, pollution controls, such as smoke control by UV light, is entered according to the user's desires. Finally, in step 2010, any other functions to be provided by the present multi-functional lighting system 100 is entered by the user. Again, as described above, all of the entry points can be provided to a user via any of the means previously mentioned.

Figure 21:
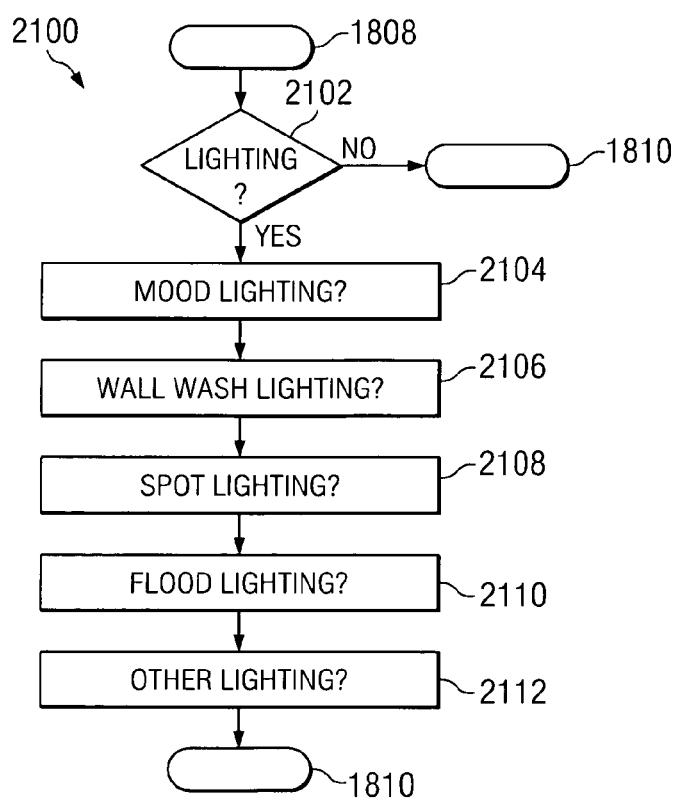
FIG. 21 illustrates in block flow diagram form a process for determining the type and number of lighting elements of the present multi-functional lighting system.

FIG. 21 illustrates a further method 2100 related to step 1808 for determining the types and numbers of light emitting elements 206, 208, 306, and 324 based on the information provided by a user. In step 2102, an inquiry is made as to whether lighting is one of the functions to be provided by the present multi-functional lighting system 100. In step 2104 through step 2112, the different types of lighting inputted by the user is used to determine the type and number of light emitting elements 206, 208, 306, and 324 and light bulbs 104 and 300.

Although there has been described what is at present considered to be the preferred embodiments of the present invention, it will be understood that the invention can be embodied in other specific forms without departing from the spirit or essential characteristics thereof. The present embodiments are, therefore, to be considered in all aspects as illustrative and not restrictive. The scope of the invention is indicated by the appended claims rather than the foregoing description.

What is claimed:

1. A system for providing a desired function in an environment using high-efficiency lighting elements, comprising:
    means for selecting at least one high-efficiency lighting element for producing a desired function, the desired function including providing sterilization;
    means for tuning said at least one high-efficiency lighting element substantially disposed over said at least one high-efficiency lighting element for providing high-efficiency lighting; and
    means for arranging said at least one high-efficiency lighting element located within said environment.

2. The system for providing a desired function in an environment using high efficiency lighting elements of claim 1 wherein said means for selecting comprises:
    means for calculating an area of a portion of said environment for determining the quantity of at least one high-efficiency lighting elements to provide said desired function for said portion of said environment.

3. The system for providing a desired function in an environment using high efficiency lighting elements of claim 2 wherein said means for selecting further comprises:
    means, responsive to said calculated area of said portion of said environment, for determining said at least one high-efficiency lighting element for providing the desired function in said environment.

4. The system for providing a desired function in an environment using high-efficiency lighting elements of claim 1 wherein said means for tuning comprises:
    means for adjusting the angle of dispersion of light emitted from said at least one high-efficiency lighting element.

5. The system for providing a desired function in an environment using high-efficiency lighting elements of claim 1 wherein said means for tuning comprises:
    thin film for shaping the light emitted from said at least one high-efficiency lighting element.

6. The system for providing a desired function in an environment using high-efficiency lighting elements of claim 1 further comprising:
    means, responsive to a command, for adjusting the output of said at least one high-efficiency lighting element.

7. The system for providing a desired function in an environment using high-efficiency lighting elements of claim 1 wherein said at least one high-efficiency lighting element comprises at least one light emitting element providing light in a visible wavelength range.

8. The system for providing a desired function in an environment using high-efficiency lighting elements of claim 1 wherein said at least one high-efficiency lighting element comprises at least one light emitting element providing light in an invisible wavelength range.

9. The system for providing a desired function in an environment using high-efficiency lighting elements of claim 1 wherein providing sterilization includes at least one of providing bacteriological control, biological control, pest control, and pollution control.

10. The system for providing a desired function in an environment using high-efficiency lighting elements of claim 1 wherein said at least one high-efficiency lighting element comprises at least one light emitting diode.

11. The system for providing a desired function in an environment using high-efficiency lighting elements of claim 10 wherein said means for selecting comprises:
    means for selecting among at least two different of said at least one light emitting diode of said high-efficiency lighting element, one light emitting diode of said at least two different light emitting diodes providing sterilization in said environment.

12. The system for providing a desired function in an environment using high-efficiency lighting elements of claim 1 further comprising:
    means for energizing said at least one high-efficiency lighting element for providing light to said environment.

13. The system for providing a desired function in an environment using high-efficiency lighting elements of claim 12 wherein said means for energizing comprises:
    means for supplying a peak current above the maximum forward current rating of at least one of said at least one high-efficiency lighting element.

14. A multi-functional lighting system in an environment using high-efficiency lighting elements, comprising:
    receiving means for receiving environmental information related to said environment;
    receiving means for receiving function information related to said environment;
    means, responsive to receiving said functional information, for determining a type and a quantity of said high-efficiency lighting elements for said environment; and
    providing means for providing said high-efficiency lighting elements and for providing sterilization.

15. The multi-functional lighting system in an environment using high-efficiency lighting elements of claim 14 wherein said receiving means for receiving environmental information further comprises:
    receiving environmental information selected from a group consisting of dimensional information and location information.

16. The multi-functional lighting system in an environment using high-efficiency lighting elements of claim 14 wherein said receiving means for receiving functional information further comprises:
    receiving functional information selected from a group consisting of lighting, bacteriological control, pest control, and pollution control.

17. The multi-functional lighting system in an environment using high-efficiency lighting elements of claim 14 wherein said determining means for determining a type and a quantity of said high efficiency lighting elements further comprises:
    determining said high-efficiency lighting elements selected from a group consisting of mood lighting, wall wash lighting, spot lighting, flood lighting, bacteriological control, bacterial control, biological control, pest control, and pollution control.

18. The multi-functional lighting system in an environment using high-efficiency lighting elements of clam 14 wherein said means, responsive to receiving said functional information, for determining a type and a quantity of said high-efficiency lighting elements further comprises:

determining a location for said high-efficiency lighting elements within said environment for providing said multi-functional lighting.

19. The multi-functional lighting system in an environment using high-efficiency lighting elements of claim 14 wherein said high-efficiency lighting elements are light emitting diodes.

* * * * *